United States Patent [19]
Hock

[11] Patent Number: 6,032,530
[45] Date of Patent: Mar. 7, 2000

[54] BIOFEEDBACK SYSTEM FOR SENSING BODY MOTION AND FLEXURE

[75] Inventor: Allan G. Hock, Londonderry, N.H.

[73] Assignee: Advantedge Systems Inc., Londonderrn, N.H.

[21] Appl. No.: 09/010,019

[22] Filed: Jan. 21, 1998

Related U.S. Application Data

[63] Continuation-in-part of application No. 08/235,486, Apr. 29, 1994, Pat. No. 5,745,028.
[60] Provisional application No. 60/036,129, Jan. 21, 1997, and provisional application No. 60/047,517, May 23, 1997.

[51] Int. Cl.[7] ................................. A61B 5/22; A61B 1/24
[52] U.S. Cl. ................................... 73/379.01; 73/379.02; 600/595
[58] Field of Search ............................ 73/379.01, 379.02; 600/595

[56] References Cited

U.S. PATENT DOCUMENTS

| | | |
|---|---|---|
| 3,791,375 | 2/1974 | Pfeiffer . |
| 4,306,571 | 12/1981 | McLeod, Jr. . |
| 4,444,205 | 4/1984 | Jackson . |
| 4,557,275 | 12/1985 | Dempsey, Jr. . |
| 4,934,378 | 6/1990 | Perry, Jr. ................... 128/733 |
| 4,984,158 | 1/1991 | Hillsman ................... 128/725 |
| 4,986,280 | 1/1991 | Marcus et al. . |
| 5,099,702 | 3/1992 | French . |
| 5,226,417 | 7/1993 | Swedlow et al. . |
| 5,697,791 | 12/1997 | Nashner et al. ............ 434/247 |
| 5,749,372 | 5/1998 | Allen et al. ............... 128/782 |

*Primary Examiner*—Max Noori
*Attorney, Agent, or Firm*—Vernon C. Maine; Scott J. Asmus

[57] ABSTRACT

A method and apparatus for monitoring key components of body movement and flexure during kinetic activities, and providing intuitive, audible, real time biofeedback to the user. The system uses one or more transducers of types that are directionally sensitive to motion, distance, velocity, and the like, or sensitive to flexure of body joints, at frequencies and magnitudes consistent with human physical activities. Universal appliances aid in the ready emplacement of transducers at user selected points on the body, with user selected orientation. Transducers are connected by wires or wireless means to a small, battery powered signal processor and biofeedback module worn by the user. Individual or integrated transducer outputs are processed to obtain the selected parameter, such as speed of rotation or degree of flexure, and measured against a multistep scale of preferably 3 to 5 steps calibrated to the range of interest and separated by perceptible difference in value. Each step triggers a respective audio tone, each successive tone preferably separated by 1/3 to 1/1 octave in pitch, the highest pitched tone triggered being held for preferably 0.1 to 0.3 seconds. Additional outputs in other forms may be provided for accessory presentation or recording devices. Sports training for improved form, such as for golf and tennis, and medical monitoring applications, including injury avoidance and rehabilitation, are among its uses.

15 Claims, 16 Drawing Sheets

BIOFEEDBACK SYSTEM FOR SENSING BODY MOTION AND FLEXURE

This application is a continuation-in-part to U.S. application Ser. No. 08/235,486, filed Apr. 29, 1994, now U.S. Pat. No. 5,745,028, and claims priority to material in Ser. No. 60/036,129 filed Jan. 21, 1997, and Ser. No. 60/047,517, filed May 23, 1997, all by the same applicant, and all pending on the date of submission.

BACKGROUND OF THE INVENTION

1. Technical Field of the Invention

This invention relates to instrumentation for biofeedback of body motion and flexure during kinetic sport activities and for medical monitoring purposes including injury avoidance and rehabilitation. In particular, it relates to a system of body motion and flexure sensors and specialized audible and other biofeedback capabilities, with controllable sensitivity and contemporaneous feedback characteristics, having broad application for monitoring various body movements and joint flexures and capturing or signaling absolute, relational and rotational body motion parameters of distance, velocity and acceleration.

2. Description of Prior Art

Motion sensors for kinetic activities such as golf, tennis and the like have long been known. The use of audible feedback to indicate level of accomplishment to the user via pitch, duration or the modulation of either, are frequently used. For example, Harrison, U.S. Pat. No. 2,064,603 describes an audible metal snap switch in the form of a wrist mounted pressure sensor worn to detect wrist flexure relating to the swing. Pfeiffer, U.S. Pat. No. 3,791,375 describes a sensor attached to a user's foot in order to detect excessive force placed on the foot during motion. Obenauf, U.S. Pat. No. 4,502,035, describes a motion sensor that is mounted to the hat of a golfer for providing audible tones to a headphone worn by the golfer, the tones indicating characteristics of the golfer while swinging the club.

Evans' U.S. Pat. No. 3,270,564, Sep. 6, 1966, is a golf club instrumented to provide an electrical signal which is a continuous function of the motion of the club and an output plot of the resulting motion. Fink's U.S. Pat. No. 3,808,707, May 7, 1974, presents a physical training system that provides an audible signal indicative of an analog of a predetermined physical activity in the manner of a musical metronome. Hammond, U.S. Pat. No. 3,945,646, Mar. 23, 1976, instruments a golf club with multiple accelerometers to indicate the precise position of the golf club at the instance of impact when striking the ball, and introduces the concept of wireless transmission of the data to a remote receiver for analysis and presentation via crt screen and/or printer.

Fletcher, U.S. Pat. No. 3,972,038, Jul. 27, 1976, introduces an accelerometer and telemetering transmission link all of which fit into a ring worn on the finger of the user. Barasch, U.S. Pat. No. 4,094,504, Jun. 13, 1978, places reeds on a tennis racquet to provide an audible tone when wind passes over them. James, U.S. Pat. No. 4,110,918, Sep. 5, 1978, offers a biofeedback training system with portable, self-contained modular units for preprocessing and storing data.

Wilhelmson, U.S. Pat. No. 4,346,363, Aug. 24, 1982, discusses a unit that produces an audible tone where the frequency is a function of the direction of the measured force and the intensity of the sound is proportional to the magnitude of the force. Whiteneir, U.S. Pat. No. 4,660,289, Apr. 28, 1987, senses joint position with an indicator that attaches to adjacent body members and measures relative position. Matthews, U.S. Pat. No. 4,867,442, Sep. 19, 1989, discloses a device worn on the head with sensors place about the headband to feed a microcomputer heart rate, time and exercise related inputs.

Smithard, U.S. Pat. No. 4,906,192, Mar. 6, 1990, employs sensing of forces generated at the foot of a boot mounted on a ski, and generates a CRT display of a simulated track that would result from the activity, for training purposes. Wilhlem, U.S. Pat. No. 4,991,850, Feb. 12, 1991, shows an instrumented golf club hardwired to a wrist worn indicating device. The display indicates the characteristics of impact (impact, club acceleration, direction, etc.) as a result of the measurements made during this action.

In general the prior art deals with systems that measure specific actions of an athletic activity. The are implemented in ways that do not lend to generalization (e.g. limited to a specific motion of the head).

Many of the systems provide feedback to a display, or in the case of audio feedback, a single tone or a continuously modulated pitch or duration of the tone is used. In actions that occur quickly, whether they be a fast 0.05 second duration of a baseball swing or a slow 0.25 seconds for a golf swing, tonal feedback does not convey the information in an easily remembered fashion and it is sometimes difficult to figure out just what happened.

Some of the cited inventions work by comparing predetermined stored information to that of the user as a specific tempo. This limits training objectives to third party standards that have no connection or relevance to the user's own unique body characteristics, style, condition and experience.

Some prior innovations are premised upon transmitting information to a base station for processing and display. This is a useful training tool, but it lacks the impact and natural benefit of instant biofeedback that is comparable to the normal response time of the body's own nervous system.

Numerous other kinetic sensors are described in various patents to provide information concerning a user's kinetic activities. While audible feedback has been used, it has largely been to indicate the occurrence of an event, (i.e. your downswing has started, your wrist has flexed properly) rather than to portray a contemporaneous "signature" or feel for the total event. The multiplicity of proposals for such systems, and the limited availability of such systems in the commercial market, demonstrate both the need for a convenient, reasonably priced, general purpose, informationally-useful sensor and biofeedback system, and the apparent difficulty of realizing this goal. The present application is directed to such a system.

SUMMARY OF THE INVENTION

The invention, in its simplest form, is a personally worn biofeedback system which uses special sensors, sensor appliances and electronic processing to convert selected motions of body members and joints into a unique, multi-tone presentation of range of motion information for self-teaching, coaching, warning and medical monitoring. An apparatus of the invention generally includes three elements; transducers, appliances, and an electronic processing and biofeedback module.

Transducers

The system utilizes one or more transducers mounted at points of interest on the body of the subject. The transducers are small and lightweight. Directionally responsive motion detectors sense motion, direction of motion, distance, velocity, or acceleration at any point of the body. Flexure detectors sense bending or flexing information as occurs at or near a skeletal joint. Sensors can be used singularly or in combination to monitor parameters of interest. Other transducer types and styles, existing or as may be developed, can be integrated into the system.

A motion detector transducer of the present invention is preferably formed from a rectangular strip of Kynar piezoelectric film laminated to a thin slab of plastic material of corresponding shape and mounted in cantilever fashion. In particular, the directionally-sensitive transducer described therein is formed from a Kynar piezoelectric film that is approximately 1 3/8 inches long; 0.42 inches wide; and 0.005 inches thick. It is adhesively secured to a strip of Mylar material that is 0.010 inches thick, and of a length and width the same as that of the piezoelectric material.

The resultant laminate is mounted in cantilever-fashion to a mounting block secured to the transducer housing. The transducer has a resonant frequency on the order of from 20 to 40 hertz. This provides a signal of sufficient strength as to enable the requisite signal processing to be performed by electronics of reasonable complexity, bulk and cost. It covers the frequency range of interest in many kinetic applications, such as in sensing golf strokes, rehabilitation exercises and the like.

The transducer may be shifted to a higher resonant frequency, e.g. on the order of from 100 to 2000 hertz, by "loading" the transducer, e.g. by applying adhesive paste to it to increase its moment of inertia and thus its resonant frequency. However, this is achieved at the expense of reducing its sensitivity. This may, nonetheless, be acceptable for applications such as measuring a baseball swing or others where substantial acceleration occurs.

An external flexure sensor may be used. It can consist of a strain gage instrument beam, piezoelectric sensor or other means for measuring flexure over a relatively large area. In the current embodiment, Kynar piezoelectric film is used and the sensing area is approximately 0.4 by 1 inch. The area measured can be extended by increasing the beam dimension, the sensing dimension or both. It is also possible to instrument the beam with other variable resistance elements, magnetic systems and the like, all within the scope of the invention.

Separate sensors can be integrated to act as a composite subsystem that allows the user to integrate several characteristics of an activity into a cohesive feedback message. This capability allows for the undertaking of relatively complex activity analysis. An example would be to measure arm movement, hip rotation, and weight transfer during the same swing. The system can literally be set up to play a tune that provides a single holistic indication of a very complex activity.

The system can utilize a local wireless communication link to interconnect the sensors and the biofeedback main module. This permits a greater degree of freedom in the placement of sensors. As an example, a first sensor is placed on the back of a glove, a second sensor, this one physically integrated into the biofeedback module packaging, is mounted on the hip. The first sensor communicate in wireless fashion to the biofeedback main module, the second one by its hard wired connection, and the module generates the particularized audible tone pattern that is a function of the timing between the motion of the gloved hand and the rotation of the hips, a very important golf or baseball measurement.

A simple static overlay switch and cable mechanism triggered by flexing motion in excess of a threshold amount is incorporated into a dynamic sensor assembly, providing a reset or absolute reference signal capability to the information stream.

Appliances

The mounting system for sensors utilizes multiple components to provide the universality of attachment appropriate to the invention's wide range of application. The principle components are a Velcro™ type or equivalent hook and eye material on one surface of the system housing, a universal mounting clip with a similarly configured surface, and stretchable or adjustable belts with or without strategic mounting surfaces configured with mating Velcro™ type hook and eye material, and/or with one or more sensor pockets with various orientations.

A range of belts and adjustment in belt sizes is necessary to allow for any sized person to be fitted around the circumference of their limbs (arm, leg, foot or hand) or trunk (waist, neck, hips, or head). The basic system module housing may be attached directly to the belt by means of the hook and eye material, or by using the clip. External flexure sensors are installed in pockets or attached by means of a trident base element that clips under or through the belt.

Another belt can be in the form of a watchband, with a buckle to affix the sensor system as one would place a watch. The system module and universal mounting clip combination can also be clipped over the waist band of the users trousers, over the side of a shoe or over the visor of a cap.

For internal directional motion sensors, a directional arrow is provided, pointed in the direction in which the measurement is to be made. The user-adjustable orientation between the system housing and the mounting clip offers important advantages of flexibility of the mounting means, allowing near infinite orientation capability. These benefits all work to allow the user to experiment freely to achieve the desired training or medical monitoring result.

Biofeedback System Module

A basic system of electronics, and optionally an internal transducer, are housed in a small biofeedback system module of less than two cubic inches volume and less than two ounces in weight.

The audible step tone biofeedback scheme of the invention is generated in the module, and is a novel method of presenting information about small, subtle increments of body movement, in real time, in a closely corresponding manner that requires little interpretive effort.

A tone generator provides instant, audible feedback. It is divided into monotonically increasing pitches. The pitch of the tones increases stepwise with preferably a 1/3 to 1/1 octave spacing so that they are easily differentiable by the user. Any number of pitches or tones above 2 is usable, however 3 to 5 is optimum for most applications because the user can recognize, distinguish and remember the different pitches.

The module housing the battery and the bulk of the electronics has been designed to a size that is unobtrusive, and can be fitted with a hook and eye material surface or other means for ready attachment directly to the appliances or elsewhere on the subject's clothes.

Further, the system has multiple motion or flexure sensing thresholds that correspond 1 to 1 with the pitches so that the incremental amount of change of position, motion, acceleration or flexure is easily associated with the pitch. The spacing between these thresholds can be programmed, either at the factory or by the user through a control. This allows the user to set up a system for one application, then reprogram it for a second activity. The system provides for a sensitivity control that allows the user to scale the threshold settings and set the point a which the tone will first trigger.

These capabilities allow the user to choose from among two modes of operation. The first we will call the thermometer mode as the first threshold is set to sound the lowest pitched tone when a predetermined motion, say 2 inches, has been performed. In this mode, each higher pitch of the tone would indicate an additional per cent of motion above the set threshold, 15% would be a typical motion threshold spacing.

In the alternate mode, the threshold is set to be centered on the middle tone. Here, consistency can be measured. If you mount the system on your hips for example, and take multiple swings of a striking implement, tones higher than the center indicator more motion while lower pitches indicate less motion. You achieve consistency by learning to swing so that only the third or middle tone in a 5 tone system is heard. Nonlinear spacing of the thresholds are quite effective for this mode, e.g. +/−3% and +/−10% about the center point. In all cases, holding the highest pitch reached for a fraction of a second makes the difference in remembering the result as easily as a simple piano tune, and not being able to interpret or remember the feedback.

The method of mapping the steps of a motion to discrete tones and holding (for a fraction of a second) the tone representing the peak of flexure reached for during the move is optimum for remembering what happened and when it happened during a move. Our research has shown that for either simple or complex movements of a monitored joint, that it is impossible to understand or remember what has happened if the tone modulation is continuously following the activity signal. However, these motions are much more memorable if the tonal feedback is divided into a range discrete steps such as a scale of piano notes. This discreet tonal feedback is a significant part of the disclosed invention contributing strongly to the users ability to remember the maximum amount of motion or flexure achieved in an action.

The feedback is instant, this is an important attribute for sports training or medical monitoring, as well as for sounding a warning when a potentially injurious move is about to be performed. Testing of the system has shown that the user develops an awareness of improper moves and quickly learns to avoid them so that the required training period to break a habit or learn to avoid an undesirable movement becomes very short.

Finally, the characteristic of the measurement can be tailored by programmed signal processing to be optimized to the need at hand.

Advantages

The cited systems either singly indicate. 1) improvement of a pattern of motion, or 2) provide a warning of an excessive or improper motion. The invention disclosed herein can provide both types of feedback for the same activity and distinguish audibly between the type of indication.

What has been invented is a generalized system of body motion monitoring and biofeedback The design allows for mounting or attachment of sensors to any accessible location on the body and at any orientation of motion or flexure. This allows use in multiple activities, multiple events within an activity, or for physically different individuals.

For example, in running where by choice the user can work to improve stride consistency, or limit vertical lift of his center of gravity, or chose to set a warning of excessive impact, or other measures of tiredness such as excessive shoulder rotation. These are accomplished by simply changing the point of mounting of the sensor orientation and sensitivity.

The invention can be used interchangeably for but is not restricted to: golf, tennis, jogging, throwing, kicking, javelin, aerobics and other sports activities; as well as all manner of job-related or industrial physical activities; and medical monitoring of personal activities or rehabilitation exercises.

The portability of the system, and its ability to be mounted anywhere on the body coupled with the systems ability to measure in any required orientation allows the user or physician to adjust to a very specific need without having to go to a custom design, (i.e. the commercial system and the breadboard are the same unit). This means that a doctor can store a few of these systems, fit them to the patient on their first visit and send them on their way. The result is a very universal and cost effective means for injury prevention, recurrence avoidance and rehabilitation.

Similarly, application to athletics and other physical activities has the same benefits. The same sports enthusiast can use the system for tennis, baseball, martial arts, fly casting and for each application can easily optimize the set up for his particular training need.

It is the net result, or combination, of the invented elements of the system that gives true universality for sports and physical exertion activities. The mounting, adjustment and programmability, and biofeedback with it's discrete tones, tonal range, and holdover peak tone that make it work.

Still other objects and advantages of the present invention will become readily apparent to those skilled in this art from the following drawings and detailed description, wherein I have shown and described only a preferred embodiment of the invention, simply by way of illustration of the best mode contemplated by me on carrying out my invention. As will be realized, the invention is capable of other and different embodiments, and its several details are capable of modifications in various obvious respects, all without departing from the invention.

DESCRIPTION OF THE PREFERRED EMBODIMENT

Typical embodiments can be generally described as having three subsystems. The first subsystem consists of one or a series of mounting appliances adaptable for applying sensors to particular body positions or joints. A particular appliance may provide a means for mounting one or more sensors with selectable orientations at a range of points on the body and in a range of orientations, guided by a coding means. Coding can be used to cue the user to proper placement of the sensor for the particular need (e.g. rotation or flexure of the wrist).

The second subsystem is the transducer or sensor subsystem. It may have one sensor or multiple sensors which may be interconnected by wired or wireless means in any configuration (common mode, differential, bridge, mixture of these, etc.), to sense the basic parameters of interest, and cause or provide separate or integrated signals for further processing. The integration of inputs from separate sensors may occur within or external to the biofeedback module.

The biofeedback module is the third subsystem. It receives input signals from the sensor subsystem and converts that information into a particularized scheme of instant audible step tones. It may also generate and store or transmit a data stream usable or recordable by remote or accessory equipment.

A preferred electronic biofeedback module subsystem contains four main blocks, 1) signal processing (gain, absolute value, integration, differentiation, band limited functions and general frequency response customization), 2) threshold detection in the form of a ladder of discrete thresholds that can be linearly or non-linearly spaced, and whose spacing can be fixed or programmed, 3) a peak detection and hold circuit, and 4) a tone generator and audio output sub-system that sounds tones whose pitches have a one-to-one correspondence with the threshold levels. The pitch rises about 1/2 of an octave with each successive threshold.

Figure 1:
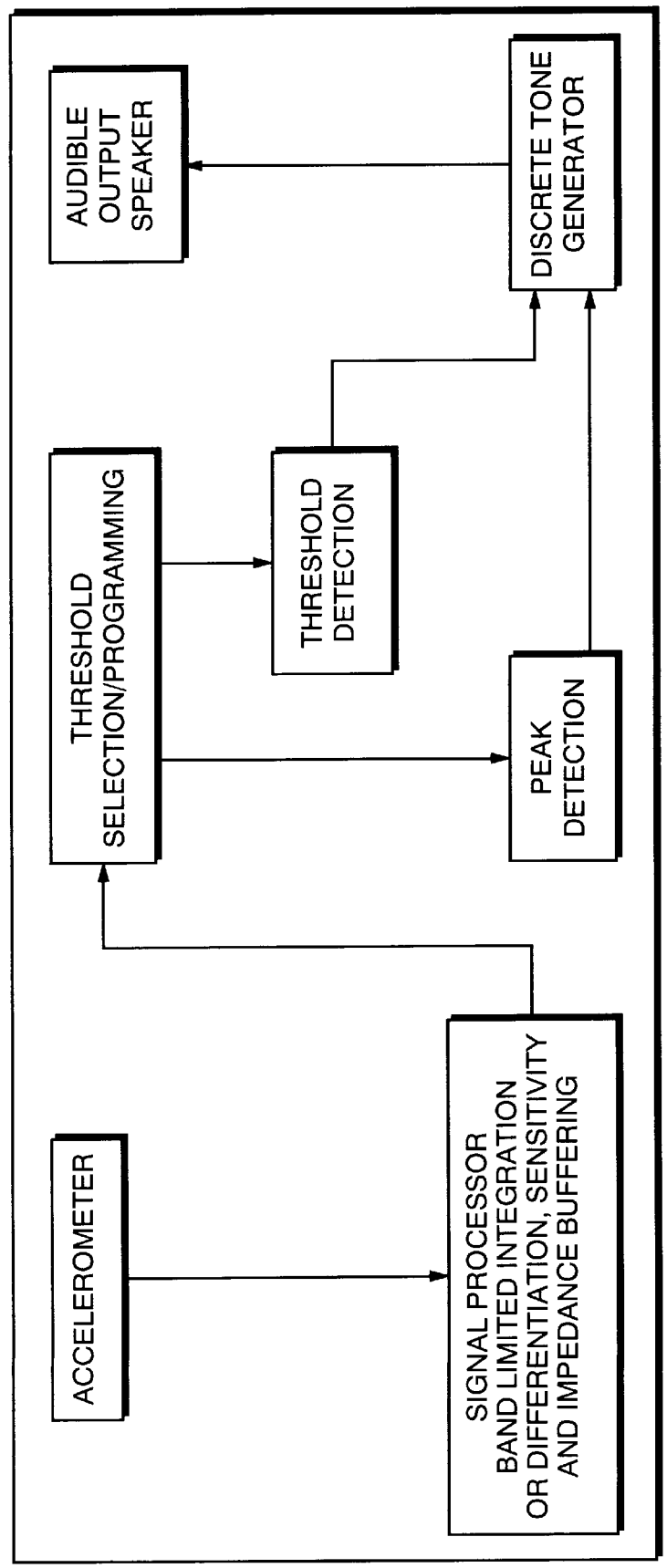
FIG. 1 is a block diagram of the functional elements of the repetitive motion biofeedback system of the invention.

Referring to FIG. 1, a block diagram of a preferred embodiment where a single sensor is housed within the biofeedback module, is presented. The block Accelerometer is a sensor or comparable element that is self referencing, in other words capable of establishing a reference independent of environment and requiring no external attachment or calibration. The accelerometer is directional, i.e. most sensitive within +/−10 degrees along a particular axis. An arrow or other indication of direction is placed on the exterior of the system housing to assist the user in orientating the device.

The block Signal Processor can be an analog circuit, a digital circuit, a microcomputer or a combination of these. It receives a signal proportional to acceleration from the accelerometer. It can perform any of the following signal processing operations: bandlimited integration or differentiation, gain, frequency response customizing, and an absolute function, and/or rectification. Signal processing can convert acceleration to: equivalent force, velocity, displacement, timing or shock.

Band limited differentiation and integration are a powerful means for tailoring the characteristic of the system to the specific requirements of the measurement. The bandwidth and other frequency response customizing parameters are considered a trade secret, while the inclusion of this feature into the system is considered patentable.

The block Threshold selection/programming includes threshold selections which can be linearly or non-linearly spaced, frequency response and nominal system gain. User programming is accomplished by switches, controls, voice command, insertion of a plug-in, etc. Factor programming is by component insertion during manufacturing, the systems are coded by color, number or other to indicate the specific program. Programming is sufficiently general to allow setup for all of the applications of a specific sport or other physical activity. A preferred functional program has five linear thresholds at 15% spacing, sensitivity/gain 40–200, and band limited integration with a BW of 3 to 30 hz. This example is ideal for use in developing a golfer's short game and putting.

The block Threshold detection detects the programmed number of discrete thresholds and sets the tone generator to the corresponding pitch. The block Peak detection senses the highest threshold that is reached and sets the tone generator to: 1) select the pitch that corresponds to the highest threshold that has been reached, 2) to turn on at the appropriate oscillation frequency, and 3) to remain on for the preprogrammed hold duration.

The Discrete tone generator generates the tone that is set by the threshold detection and peak detection circuits. It generates the timbre of the tone which can be soothing for normal feedback and raucous for warning feedback indication.

The block Audible output speaker or other feedback transducer is used to communicate the information to the user. This output can be optionally combined with: 1) a display, voice or other means for characterizing and/or recording the event.

Figure 2:
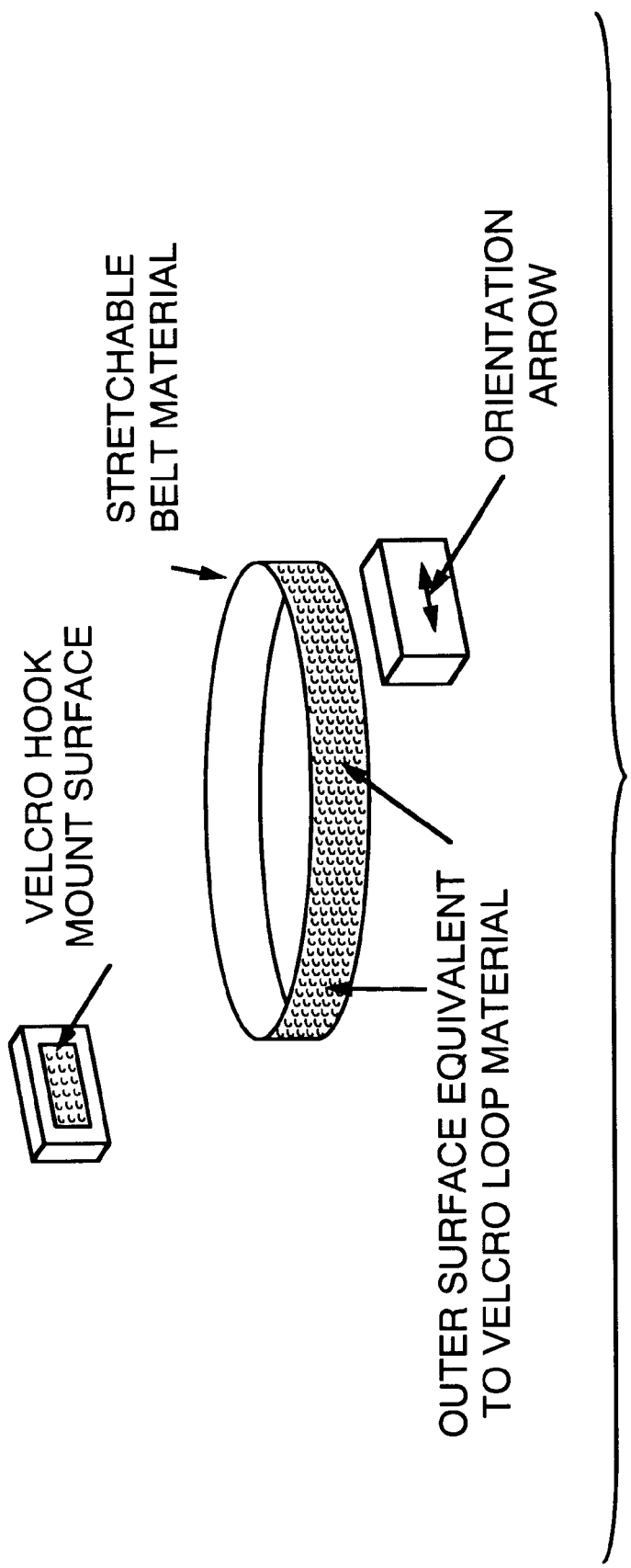
FIG. 2 is a perspective view of a mounting belt and system attachment variations that include placement for measurement of rotation.

Referring now to FIG. 2, one or two motion detection sensors, each a motion detector sensor housed within a standard module, can be mounted onto the body using a belt and compatible hook and eye material type fasteners. When two sensors are used on opposite sides of the waist belt and connected so that in processing, the signal of one system subtracts from the second system, the resulting biofeedback is a measure of rotation about the vertical axis of the subject's body.

Figure 3:
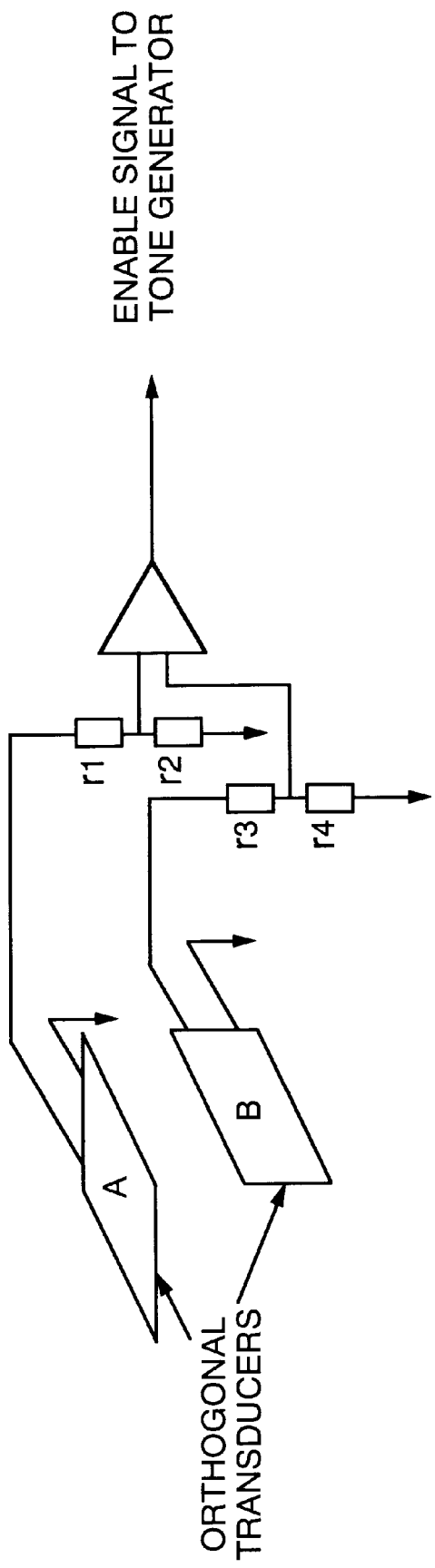
FIG. 3 is a diagrammatic view of the relative orientation of directionally sensitive transducers within the system module housing.

Referring to FIG. 3, some applications require a higher level of directional motion discrimination. This is accomplished by adding a second transducer B within the same modular housing, oriented orthogonal to first transducer A. A simple electronic circuit detects the point where the element magnitudes crossover. This provides a sharp point of angular discrimination, on the order of plus or minus five degrees.

An application example for the narrow angle measuring capability of FIG. 3, would be a tennis swing where the goal is to measure vertical lift of the racquet face in the presence of a high forward velocity. The purpose might be to allow the user to optimize the amount of desirable topspin imparted to the ball while it is being struck. A second example is a golf swing, where it is desirable to characterize elements of the swing with a high degree of discrimination of angular direction.

Figure 4:
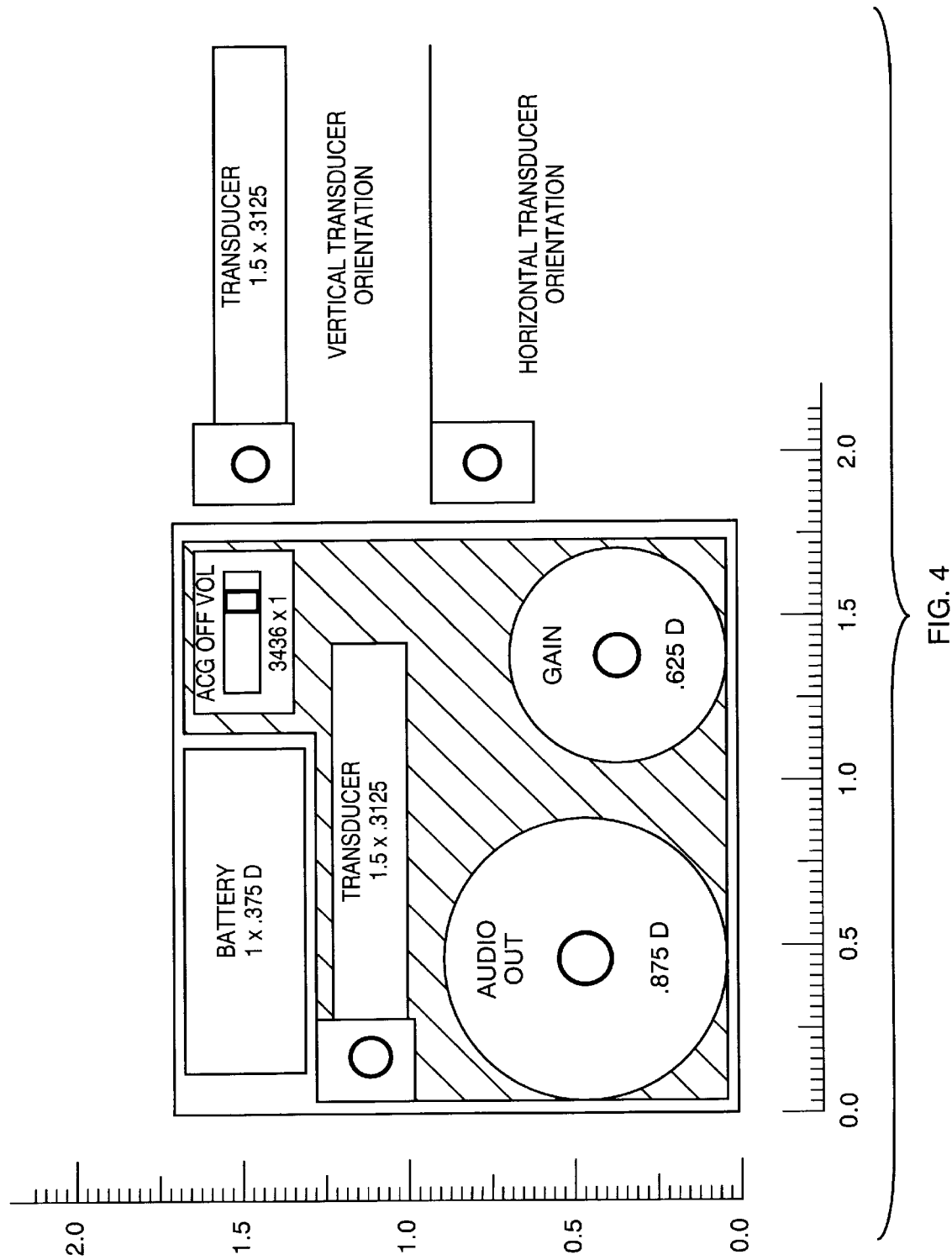
FIG. 4 is a top view illustrating the layout of principal elements of the system module.

Referring now to FIG. 4, a typical layout for a directional motion sensor system module and transducer orientation is shown. Battery, transducer, audio output element, user interface switches and a potentiometric gain and threshold selecting device, and an area of printed circuit board upon which the electronics is mounted. The back surface of the housing is fitted with a Velcro® or equivalent hook and eye material surface for attachment to a belt type of mount as shown in FIG. 2.

Figure 5A:
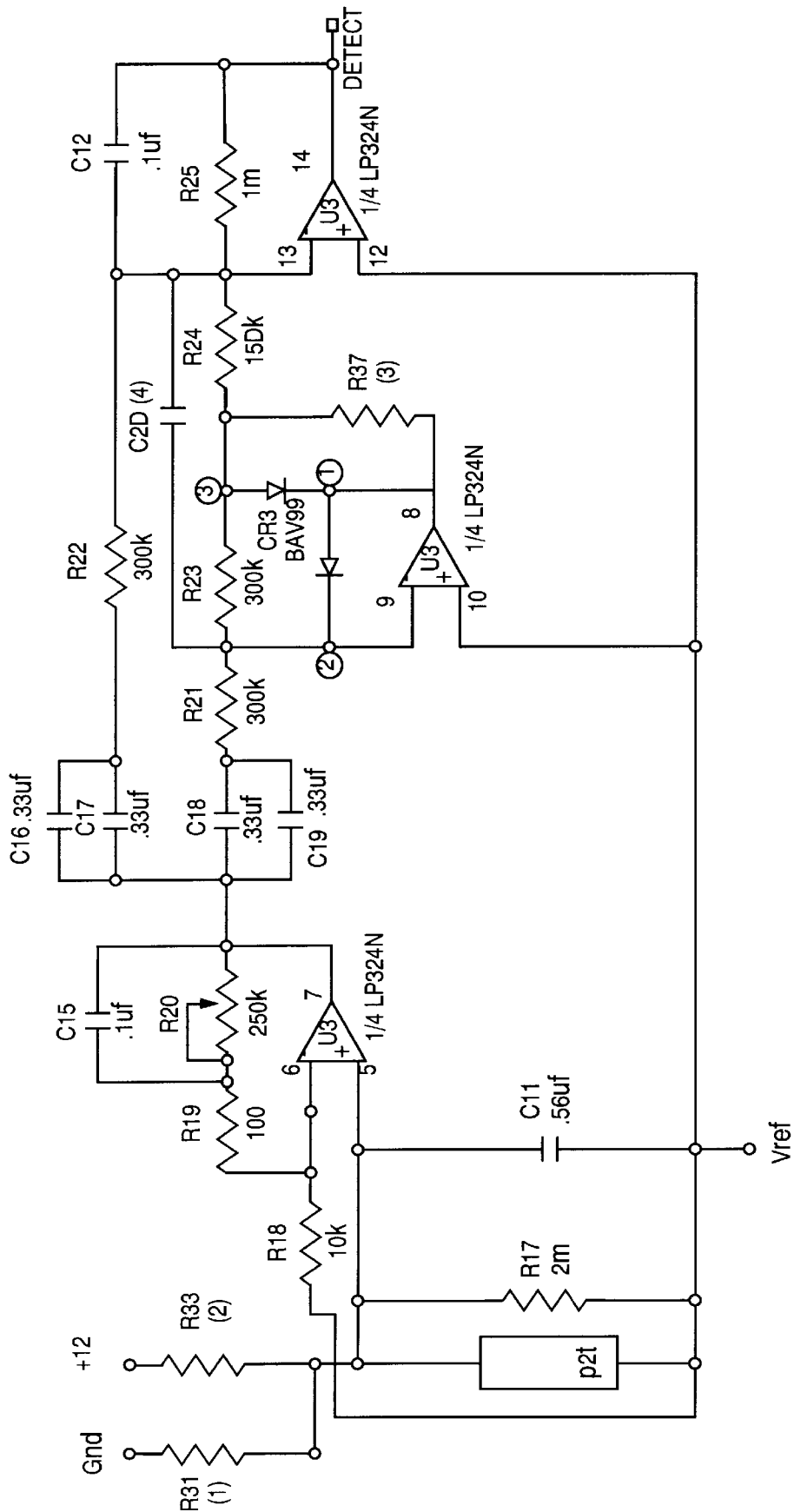
FIGS. 5A and 5B are a schematic diagram of the circuitry of the preferred embodiment.
Figure 5B:
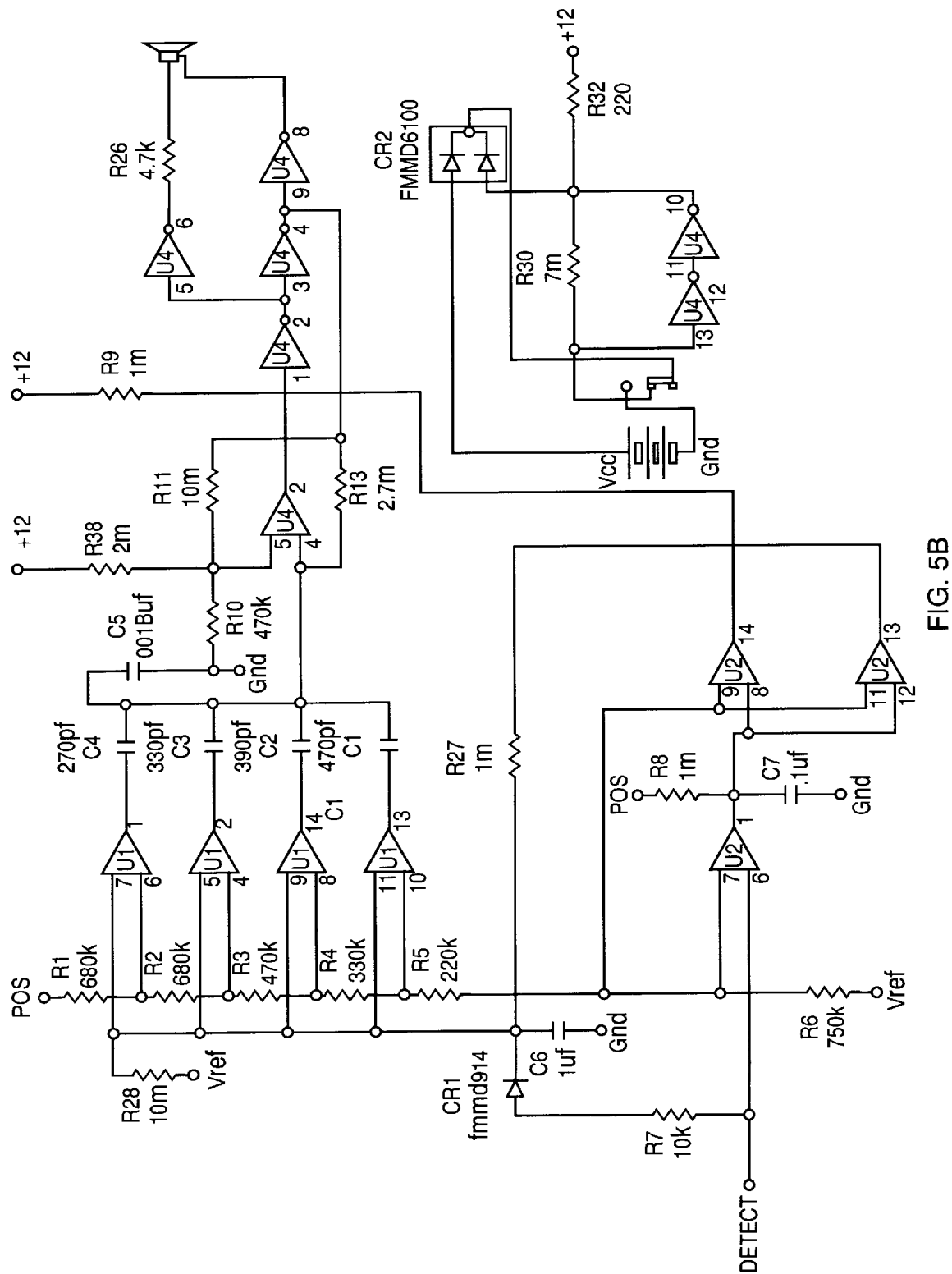

Referring to FIGS. 5A and 5B, the circuit of the preferred embodiment is shown. Following is a discussion of the capabilities which is in turn followed by a discussion of the various components that effect circuit behavior and their specific functions.

This circuit is capable of being tailored to an number of applications for each transducer type and further, is designed to accommodate several different transducer types and configurations. The configurations that can be selected by component placement within the same PCB topology are full bridges, half bridges, and single elements. These configurations can be self exciting or can be biased with current or voltage.

The circuit contains three stages of gain, all shown in FIG. 5A. These stages can be arranged by diode selection and placement to be linear, absolute value or to have a positive or negative halfwave rectification characteristic.

The transfer function in the frequency domain can be adjusted to accommodate the needs of the various intended applications. There is a high degree of independence between the numerous poles and zeros that can be inserted or deleted by placing or leaving out a specific component (many of this relationships will be discussed later in this section). The corner frequencies of the various poles and zeros correspond to component value selection.

The discussion of the specific relationships between function and component value for the front-end circuit shown in FIG. 12a follows:

1) R20/R18 sets the gain of the first stage.
2) R21, R22, R23 and R24 set the gain of the second stage.
3) R25/R24 sets the gain of the third stage.
4) R17 in parallel with C11 match the sensor system input impedance and provide a low frequency rolloff.
5) C15 provides a first high frequency rolloff.
6) Diodes, when CR3 is a BAV99 component, the circuit provides an absolute value function, when CR3 is deleted, the circuit has a linear characteristic, and by placing a simple between the terminals 1 and 2, or 2 and 3, halfwave rectification is accomplished.
7) R20, R25 and R37 add additional compensation capabilities.
8) R24, R22 and C12 provide a second integration corner.
9) R31 and R33 provide means for the bias configurations for the sensing system.

The second half of the circuit, FIG. 5B, consists of a multiple programmable threshold stage, a discrete tone generator that generates a pitch corresponding to each threshold. It contains a peak detection and hold circuit with a controlled hold time. There is a tone generator and an audio output stage.

The discussion of the specific relationships between function and component value for the detection and tone generation portion of the circuit follows:

1) R1, R2, R3, R4, R5, and R6 program the threshold detection steps (can be linear or non-linear) by component value selection.
2) C1, C2, C3, C4, C5 and C6 establish the particular monotonically increasing frequency of the tone generator for each tone. In this circuit from 1 to 5 tones can be generated.
3) R8 and C7 set the hold time for the peak detection stage.
4) U4 generates a peak to peak voltage that is twice the supply voltage.
5) R7 establishes the hysteresis for the threshold detection stage.

Figure 6:
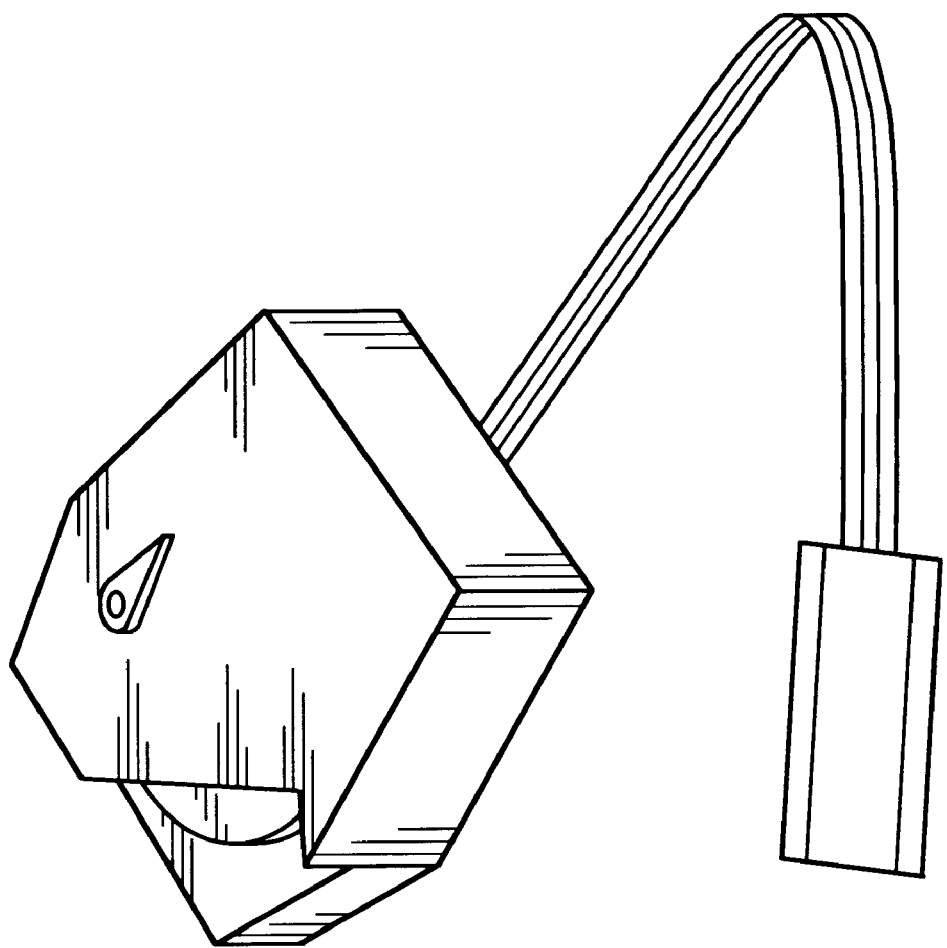
FIG. 6 is a perspective view of the body flexure system module and external sensor with flexible flat conductor leads.

Referring now to FIG. 6, the biofeedback module is housed in a pocket watch sized case. It weighs less than 1.5 ounces, and contains the circuit of FIGS. 5A and B, with electronic functions including: impedance buffer, signal processing, tone generation, sensitivity adjustment and an output transducer and battery.

An external flexure sensor is attached to the module via a suitable length flat two conductor lead. It can consist of a strain gage instrument beam, piezoelectric sensor or other means for measuring flexure over a relatively large area. In the current embodiment, Kynar piezoelectric film is used and the sensing area is approximately 0.4 by 1 inch. The area measured can be extended by increasing the beam dimension, the sensing dimension or both.

Figure 8:
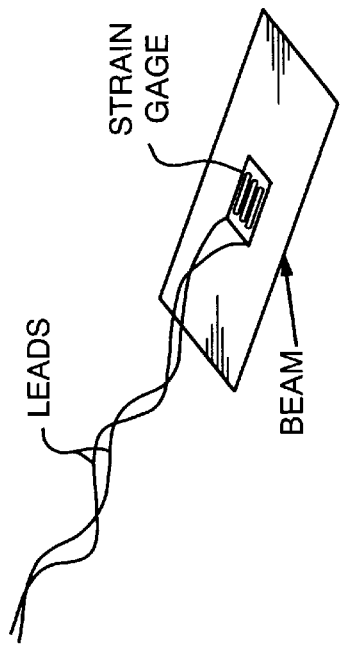
FIG. 8 is a perspective view of the components of an alternative flexure sensor configured with a strain gage on a planar beam.
Figure 7:
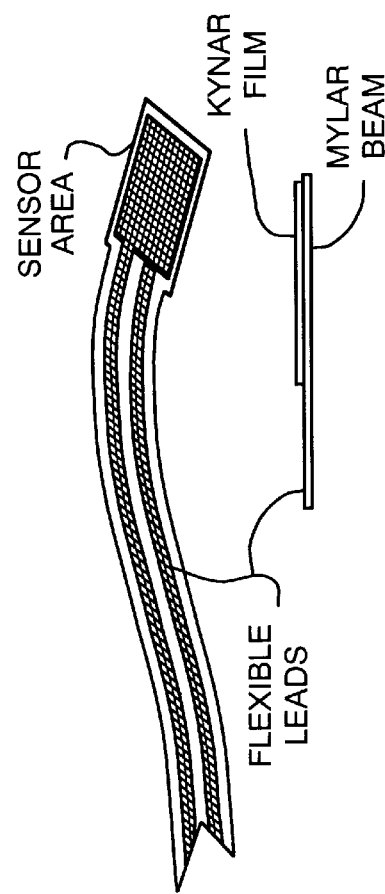
FIG. 7 is a perspective view of component parts of an external flexure sensor.

Referring now to FIGS. 7, an external flexure sensor consists of an instrumented beam which has flexible flat leads leading from the sensor element to the system module. The sensing element is a 0.4" by 1" piece of Kynar piezoelectric film laminated to a 0.005' thick mylar beam. An alternate means for measuring flexure may be used, as for example a strain gage instrumented beam as shown in FIG. 8. It is also possible to instrument the beam with other variable resistance elements, magnetic systems and the like. The instrumented beam has a resonant frequency of at least 66 hz. and a damping factor for the beam assembly of at least 0.6.

The sensors of FIGS. 7 and 8 connect to the electronic circuits of FIGS. 5A and 5B: sensor input buffering and gain, signal processing, multiple threshold sensing, discrete tone step generator, peak signal and tone holding circuit, tone generation, acoustic output transducer and battery as previously disclosed, with the exception that the signal processing profile is different. Flexure sensors tend to need much lower frequency response, zero being ideal. A range of 0.01 to 0.1 hz (depending on application) is acceptable.

Figure 9C:
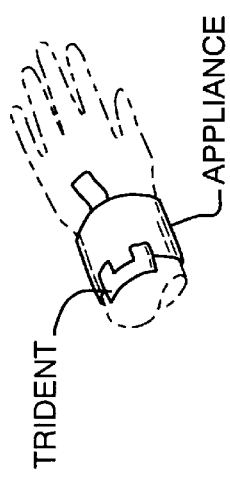
FIGS. 9A, 9B and 9C are perspective views of the sensor of FIG. 7 attached with appliances in three alternative locations; wrist, elbow, and back, respectively.
Figure 9B:
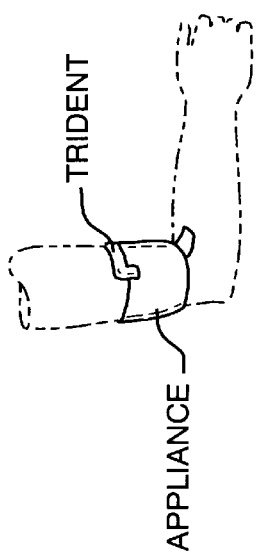
Figure 9A:
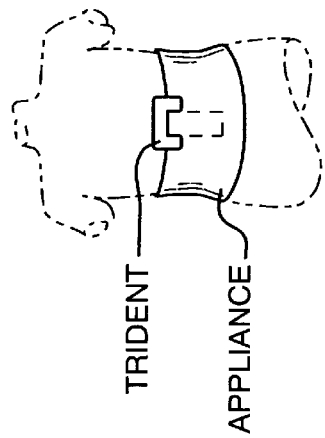

Referring now to FIGS. 9A, B and C, a mounting appliance is necessary to apply a sensor or sensors to a particular joint or point of the body for measurement, such as the wrist, elbow and back, as illustrated. This appliance is fabricated of elastic cloth material and sized for a non-slip fit on subjects within the size range.

One can expect a one-to-one correspondence between a mounting appliance and a specific joint, however, it is possible to extend the universality of an appliance to satisfy the requirements for more than one joint, for example the elbow and wrist. The mounting appliance can contain one or more receptacles, slots, pockets or the like, which when properly installed on the subject, selects the particular point or angle of flexure of a joint that is to be studied.

Figure 10:
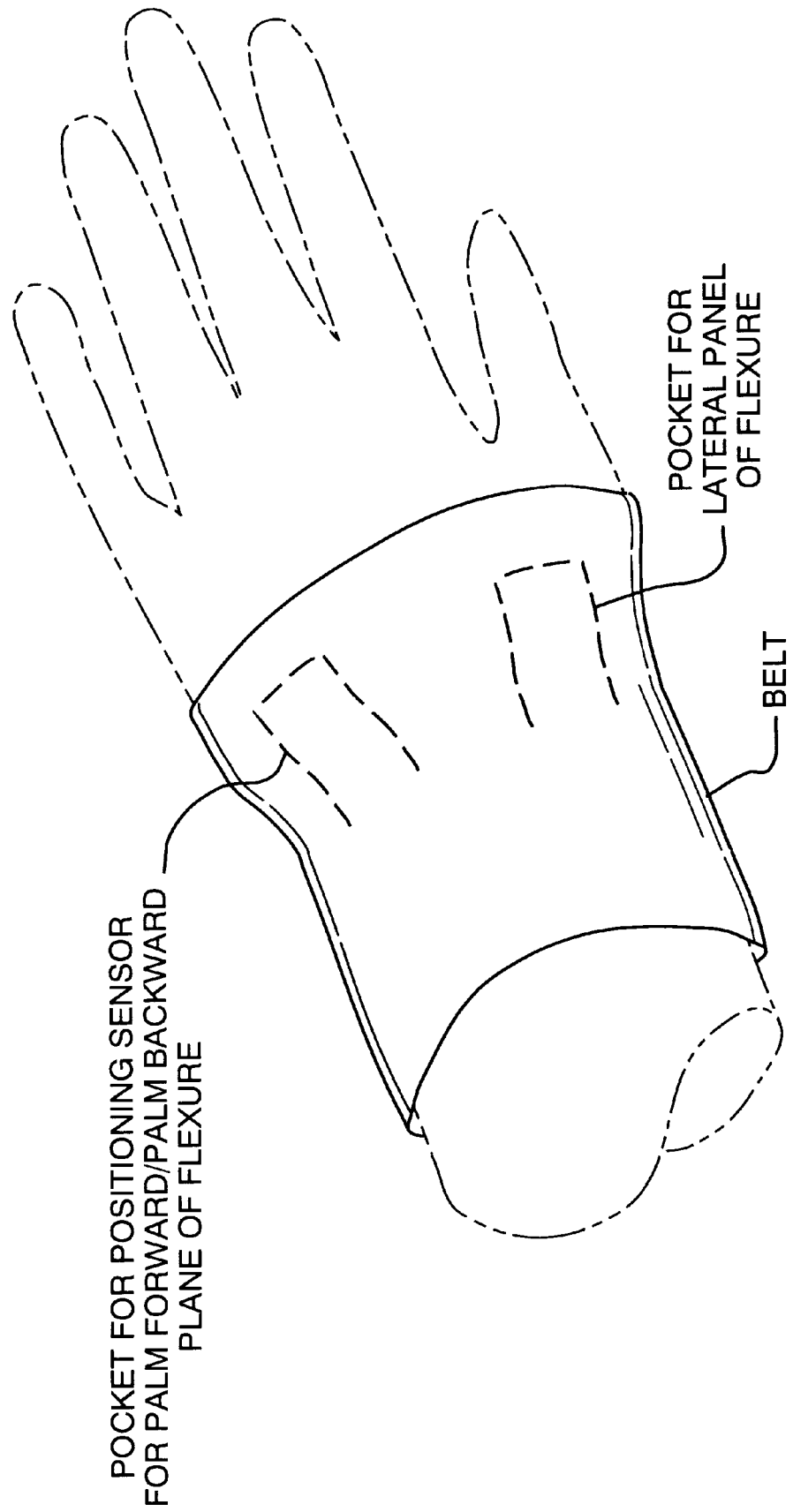
FIG. 10 is a perspective view of a wrist appliance with sensor pockets located to provide orthogonal axis flexure sensing.

Referring to FIG. 10, a multi-pocketed, belt type wrist appliance is shown applied to a wrist. The wrist is an example of a joint where many motions are possible. The appliance provides means to select between orthogonal directions of motion of the wrist. The user or physician merely fits the mounting appliance onto the user/patient, selects the appropriate receptacle for placement of the sensor, and inserts the sensor into it, where it is retained by the friction and tension of the elastic fit.

A biofeedback system module is then attached to the subject near or on the mounting appliance by Velcro or other attachment means, and connected to the sensor lead, to provide a complete self contained and unobtrusive monitoring system that is ready to operate.

Figure 11:
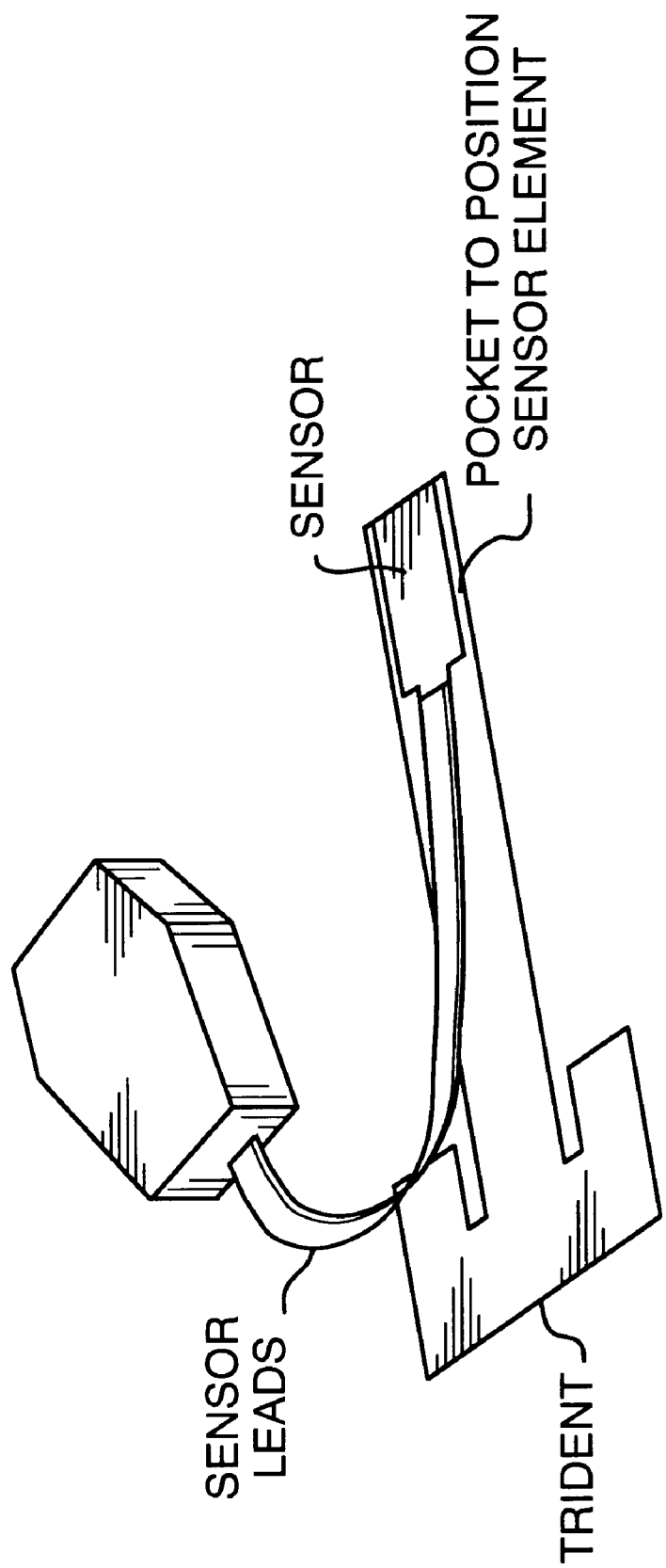
FIG. 11 is a perspective view of the system module, external sensor, flexible leads and mounting trident, with sensor installed in pocket of trident.

Referring now to FIG. 11, the sensors illustrated in FIGS. 9A, 9B and 9C are specially configured for emplacement in respective appliances by use of the trident shaped base member illustrated here. The sensor element fits into a thin pocket at the base of the trident. The sensor leads run up the base and beyond the top of the trident. The trident conveniently couples with the mating mounting appliances to consistently position and hold the sensor so that placement of the sensor's zone of sensitivity is maintained over the hinge point of the body joint being monitored.

Figure 12:
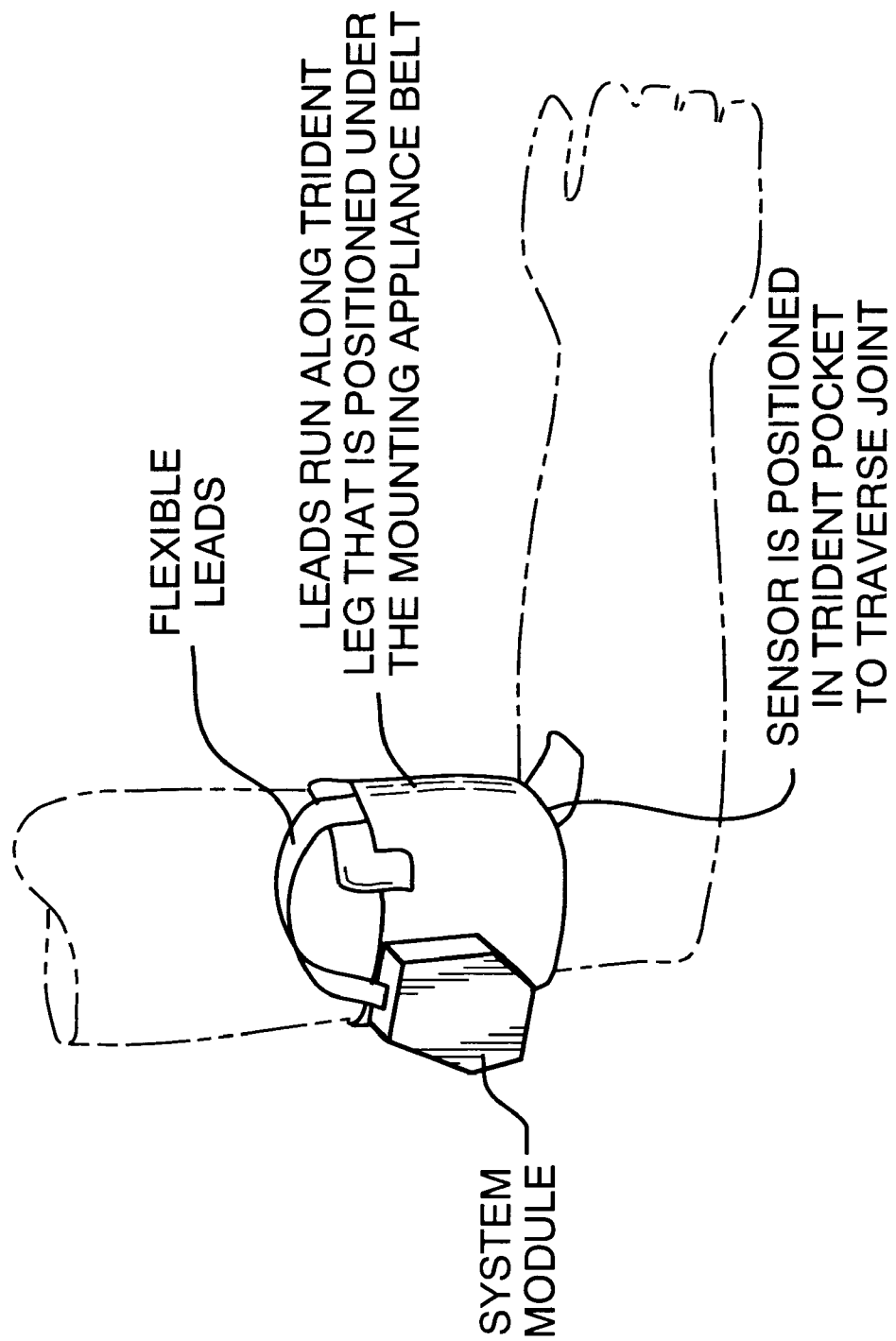
FIG. 12 is a perspective view of the system module, trident and external sensor of FIG. 11, attached to a user's elbow joint with a mounting appliance.

FIG. 12 illustrates a trident configured flexure sensor emplaced in an elbow appliance, with the system module attached to the side of the appliance.

Figures 13A, 13B:
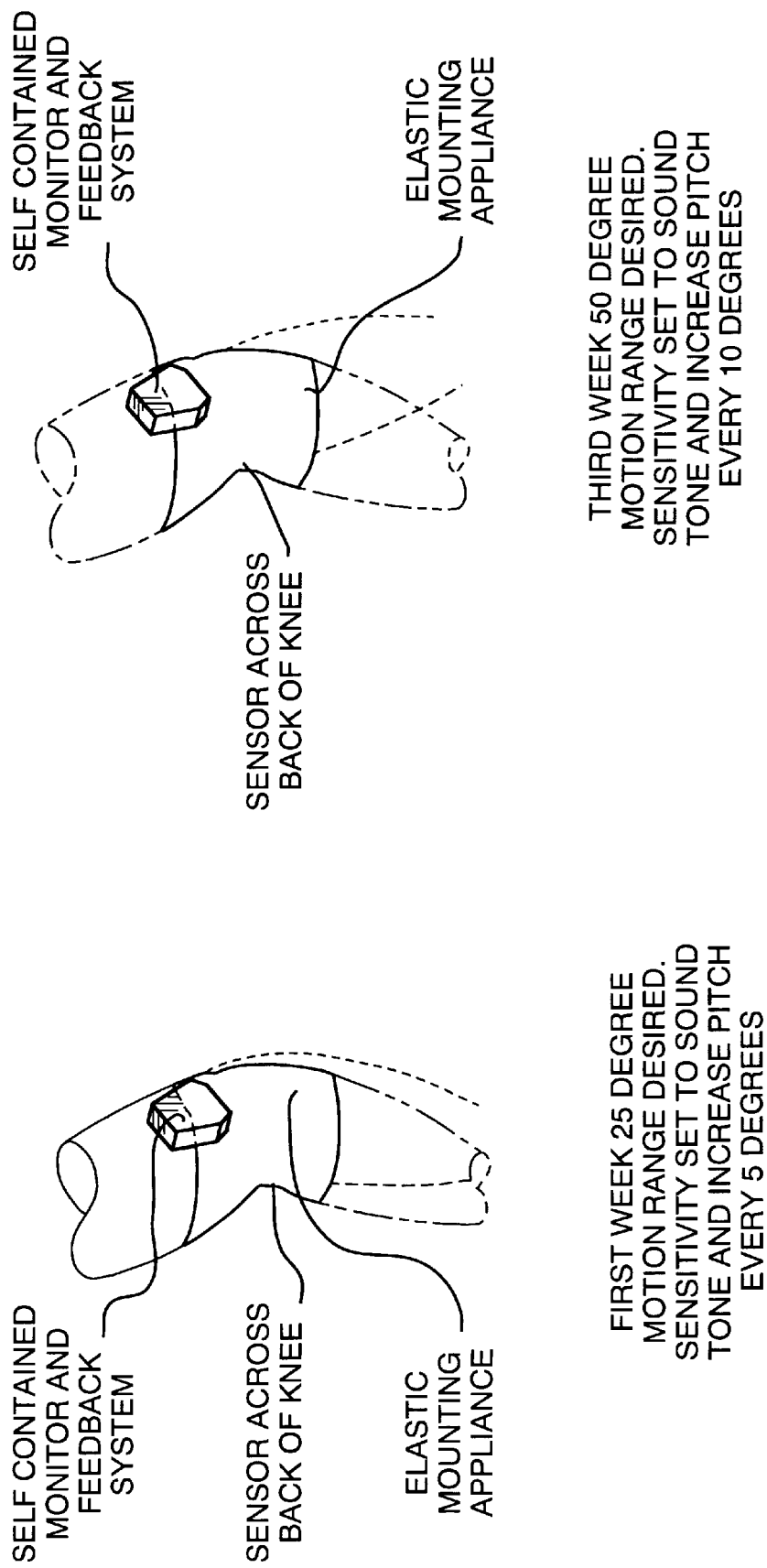
FIGS. 13A and 13B are illustrations of progressive range of rehabilitation flexure motion for a knee at first and third week intervals, as monitored by a preferred embodiment of the invention.

Referring now to FIGS. 13A and B, the invention is shown applied to a knee joint for monitoring range of motion. The sensor (not shown) is in a pocket of the appliance at the inside of the knee joint.

In recovering from various joint injuries, a rehabilitation program involving increasing range of motion over time is typical. The invention disclosed herein is particularly useful for these purposes. Once the system is set up by the attending physician, it gives audible warnings any time particular amounts of motion are performed. The range can be easily increased, say by 20% per week, by simply adjusting the sensitivity of the system a pre-determined amount. From the wearer's perspective, the apparatus of FIGS. 13A and B is little more than an elastic bandage with a 1.5 ounce instrument module attached, yet it provides all of the information necessary to avoid further injury and to help optimize the intent of the rehabilitation program.

Figure 14:
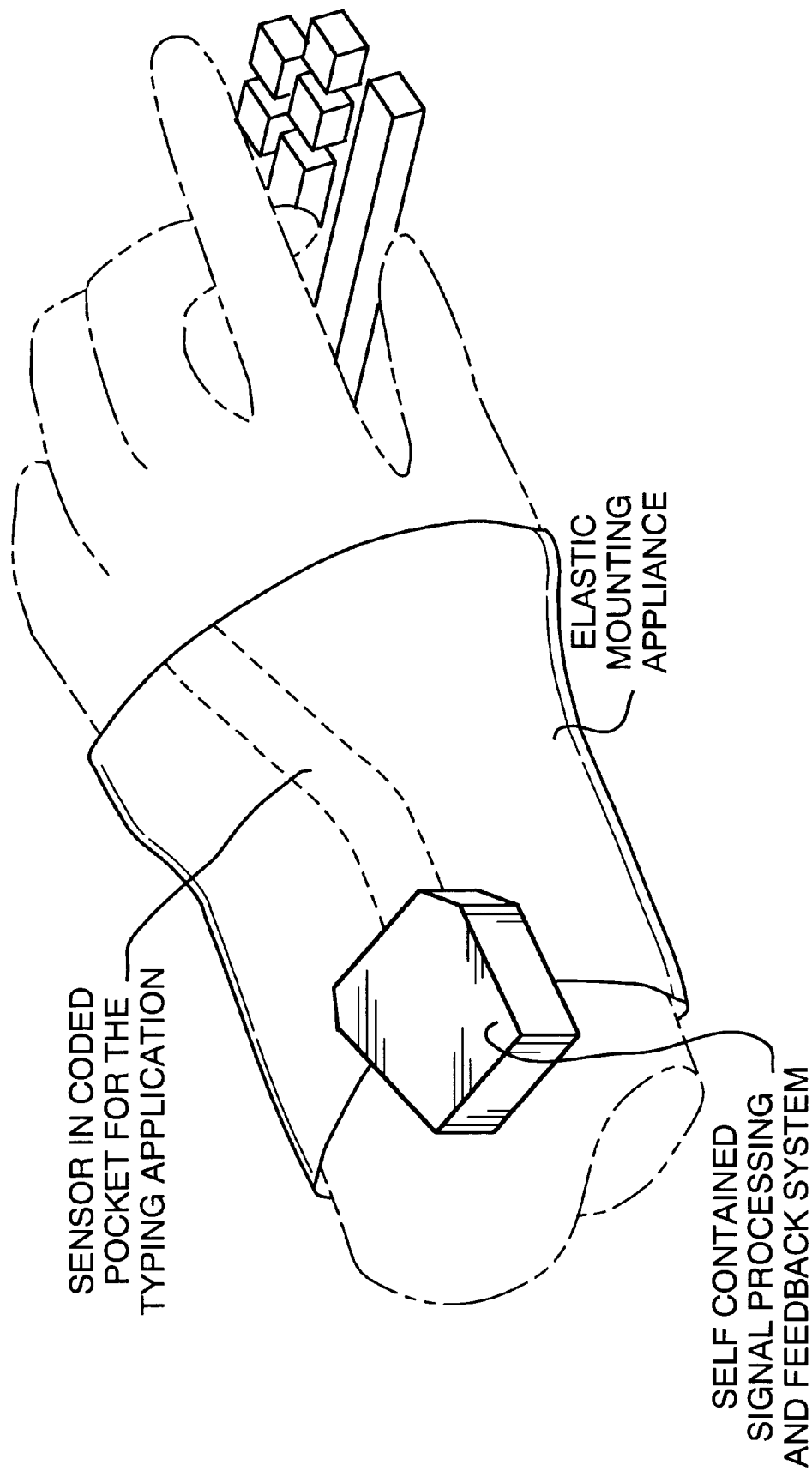
FIG. 14 is a perspective illustration of a preferred embodiment as wrist mounted for monitoring motion to avoid Carpel Tunnel aggravating movement on a keyboard.

Referring to FIG. 14, illustrated is the application of the invention to a wrist joint to monitor work-related wrist motion. It is well established that certain repetitive physical motions cause inflammation of the Carpel tunnel and can become very debilitating. Many jobs such as typists, super market checkers, hair dressers, assemblers, etc., are known to be vulnerable to this type of injury. Each of these occupations have A-priori actions that cause or aggravate the condition. This A-prior information can be used to simplify the monitoring required to retrain operators. The invention disclosed herein is particularly effective in training people away from specific motions such as these.

The wrist mounted system of FIG. 14, can be used for the flexure of the wrist of the supermarket checker, or adapted for a different wrist motion for the assembler or the typist, using the same mounting appliance and correctly selecting the coded placement of the sensor and choosing the correct sensitivity.

Figure 15:
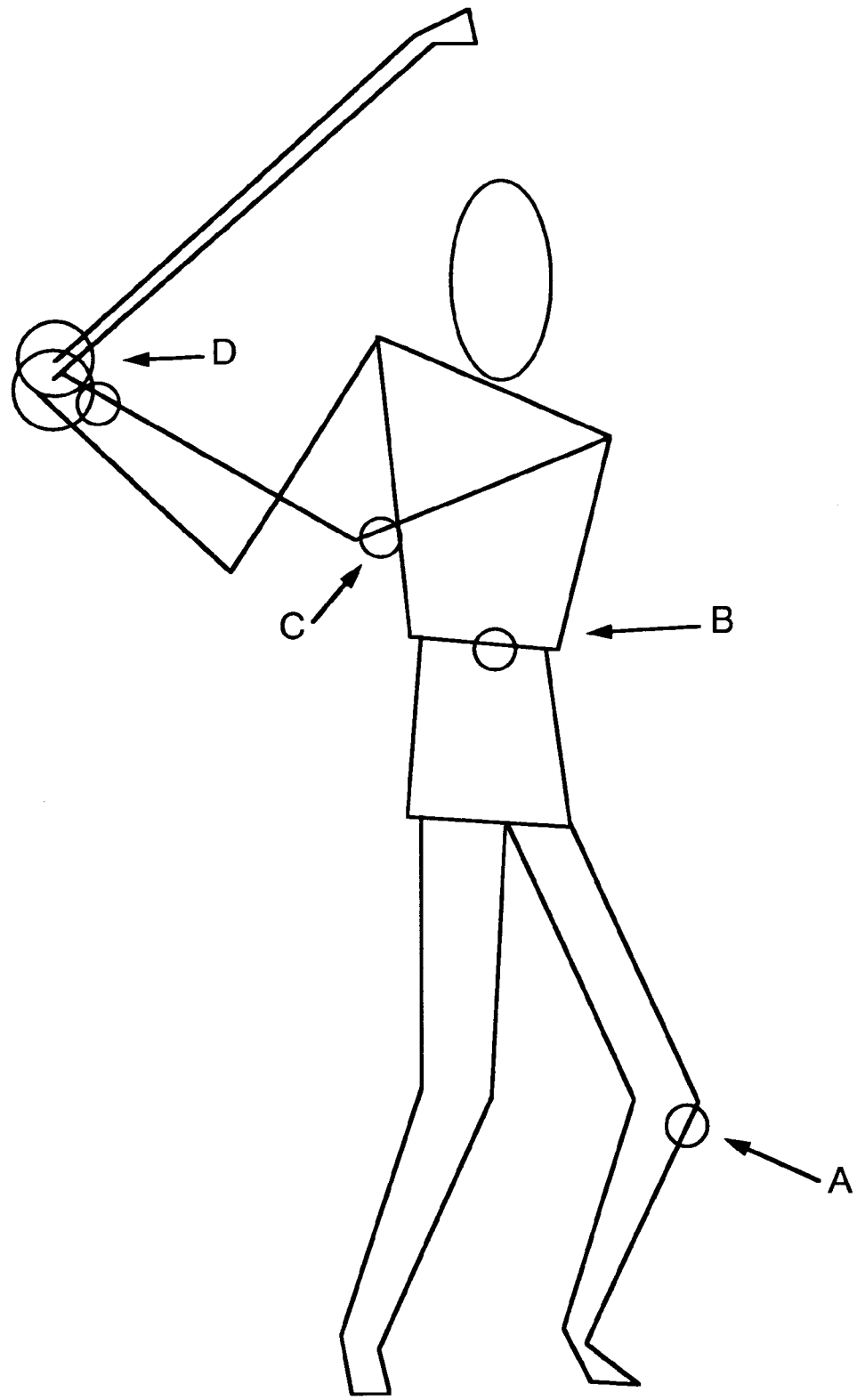
FIG. 15 is a depiction of a golfer poised to swing, identifying key points of interest for motion monitoring.

Referring now to FIG. 15, illustrated are key points A, B, C, and D of interest on a golfer poised to swing, regarding the properly coordinated motions for an effective swing. Here the user might desire to measure the time relationship and tempo of various parts of his swing. For example the sequence: 1) measure start of motion of his left arm by using sensors placed at D and C, while measuring 2) rotation of his hips by using the sensor placed at B, and 3) measuring the outward motion of his left knee, measured by the sensor placed at point A.

To accomplish the desired result, the user must orient the sensors correctly and select the appropriate program. This is accomplished as follows:

The information from sensors at points A, B, C, and D, may be selectable to permit feedback that is a function of any number or combination of the sensors. This example shows how mounting flexibility and choice of program enables the user to accomplish very sophisticated measurements using simple steps. As examples of mounting facility, a combination of watchband and belt style mounts are called for. Mount choices might be as follows: he might have the left arm sensors mounted on his left wrist (D) and elbow (C), using a watchband mount, while using a belt mount around his waist, to measure hip rotation at point (B), and finally an elastic band type mount worn on the left knee to mount a sensor device at position (A).

Recall, it was assumed that the user knew what program and locations he would choose for the required measurement. Frequently this is not the case, often the user is unsure of the correct or optimum location for the sensors. Also, he may not be aware of the best program selection for maximizing his training progress. However, the latitude for experiment afforded by this system's flexibility advantage makes it possible to converge on an excellent program. Since simple means is provided for reorientation of the sensor and device reprogramming is equally simple, the user is presented with a simple experimental environment. This is a major advantage of the invention disclosed herein, whether for recreational or medical reasons. The user can use simple trial and error methods to arrive at a program that works and is best for his particular training or monitoring needs.

The system as described above, to this point, is a dynamic system. Motions to very low frequencies (as low as about 0.01 hz.) can be measured but the system will not remember a static setting. It is common practice to use signal and or integrator reset circuits to yield quasi-static or quasi-d.c. response from systems where drift, integration of offsets and a.c. coupling preclude true static (zero frequency) response. Reset switches are commonly used. However, for systems that are to be worn by a patient or athlete, the solution must be unobtrusive and comfortable to wear.

Figure 16:
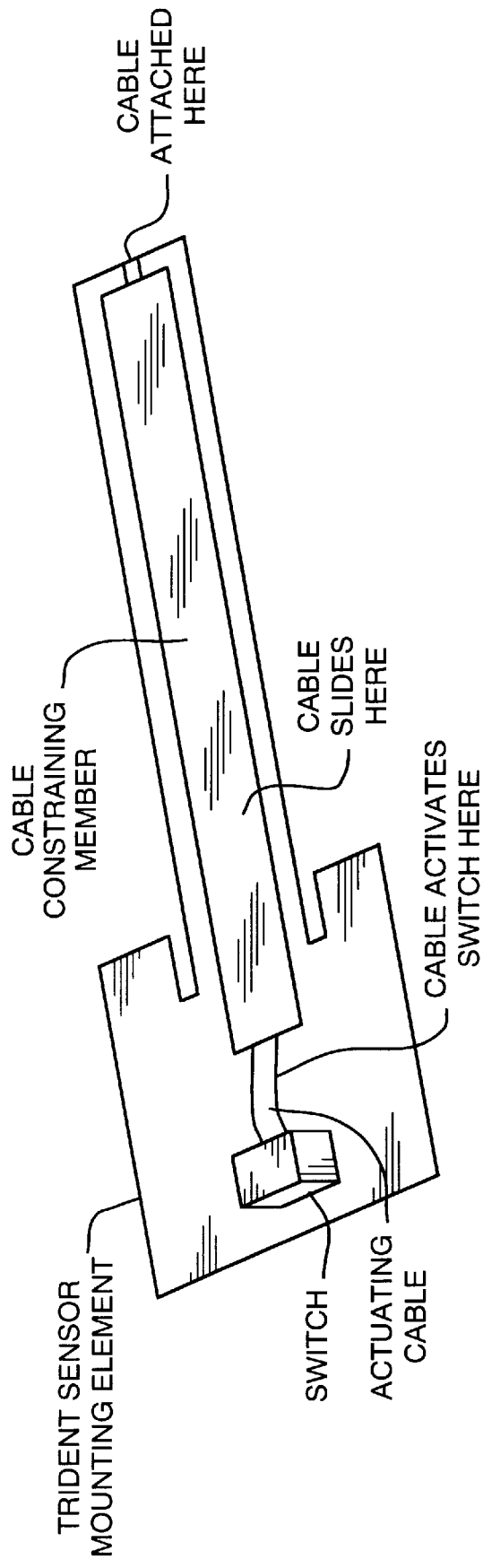
FIG. 16 is a perspective diagrammatic view of a trident sensor mounting element configured with a switch and cable system for static sensing.

Referring now to FIG. 16, there is illustrated a constrained cable, commonly referred to as a "throttle cable", and a switch, added to the trident sensor mounting element of a flexure sensor assembly. This provides static or on/off sensing of a flexure exceeding a threshold amount to the system.

An automotive throttle cable is a well know solution for transferring motions from or to remote points. Such a cable is used here to activate the switch with a sufficient rotational displacement or flexure of a body joint. The switch could be used in turn to reset the system, or mark repetitive events of an absolute value.

What is disclosed in FIG. 16 is a design for such a switch and cable system that is both unobtrusive and comfortable to wear. One end of a switch cable or displacement motion sensor strip is attached to a distal end of a flexure sensor base element, and the other end is connected to the reset switch which is mounted at a proximal end of the base element. The trigger strip is confined laterally but can slide freely in its sheath. The length of the strip is calibrated to the length and range of flexure of the base element to provide a switching event when the base element is flexed in either direction beyond a threshold amount or boundary limit. Activation of the switch, usually a momentary contact, provides a system reference as to the time of a specific amount of flexure.

Note that the switch system of FIG. 16 can be used alone to provide a single point of reference. Also, the switch can replaced by a linear potentiometer or a linear encoder (indexed, incremental or quadrature) to function as an absolute analog system over a limited range. It is however, very effective as a low cost static overlay that is used with the sensors and circuits described above. The dynamic system provides necessary refinements of signals for early warnings to be sounded so that an improper lift is aborted or a range of motion is not exceeded. The static overlay switch inserts a static reference into the dynamic information stream and can be used to provide an absolute limit signal.

A dynamic sensing system with a static response feature could be used in place of the dynamic system in combination with the static overlay switch as presented here, but at greatly increased cost, and requiring considerably more tedious calibration means.

Examples of other sports uses of the invention include applications to baseball, golf, jogging, tennis and discus throwing. This diverse set of applications are all possible as a result of the programming flexibility including pre-programming, free choice of position on the body and free orientation of direction of measurement means developed in this invention.

Runners or joggers might use the system. In these applications, the user wears the sensor on a belt with orientation to measure along the vertical axis to sense up and down motion and shock characteristics. This trains the runner to not lift his body weight for each stride (large motions indicate expenditure of unnecessary energy). The user would set a goal to run with successively less vertical motion thus becoming a more efficient runner. To accomplish this he would select either the velocity or distance parameter and select pitch modulation for the feedback tone. Then the user would concentrate on learning to run so that the modulation of pitch is minimized during each stride. Any reduction in the pitch modulation would signal an significant improvement in that component of his stride. The choice of a continuously modulated feedback tone is an example to the system being used in the optimization mode.

In an alternative mode for runners and joggers, the user selects the shock parameter, the sensor is again oriented vertical direction and the alarm mode is selected. In this mode the feedback is given only when the threshold is exceeded. The user sets the threshold so that it just goes off occasionally when he/she runs normally, providing a boundary signal. When sufficient control is developed that the alarm tone is not triggered, the threshold setting is lowered so that it goes off occasionally at the new improved training level.

The cited sequence: 1) setting the threshold so that it just sounds an alarm at your current training level, 2) learning to run without triggering the alarm, 3) further reducing the threshold setting when step two is realized, and 4) repeating steps 1) through 3) until a desired training level is achieved, is exemplary of a new and efficient training process.

It is possible to combine the functions explained above, optimization and warning respectively, into a single unit. This more sophisticated implementation of the concepts would allow one parameter to be selected for optimization while the second is set for a warning condition. Since by nature of this concept, optimization utilizes a constant feedback tone character while warnings are normally off, sounding only when the undesired event occurs, simultaneous use is possible as the two modes are not in conflict. For example, the optimizing tone of the center of gravity monitoring would be pleasing, pitch modulated tone, while the shock warning tone though silent until the undesirable event occurs, would issue a loud annoying sound. The significantly different character of these two feedbacks would avoid confusion.

A priority will be imposed naturally, as the alarm's warning-like character will overtake the pleasing nature of the optimizing tone when conditions warrant such an action. This use of two noncompeting signals to allow simultaneous monitoring for optimization and protection without compromising performance is considered a unique feature and advantage of this invention.

Novice tennis players frequently will run to the spot where the ball is going to land and then try to jerk the racquet back in a hurried manner to strike at the ball. Teaching professionals coach beginners to bring the racquet back immediately, moving it to a semi-cocked position as soon as they spot where the ball is going to land.

By doing this as they start to run for the ball they do not generate a jerky motion. They develop a smooth forward swing, starting from a the more prepared and desirable position. By employing the sensing and biofeedback signals of this invention they are able to learn this simple but important tactic much more quickly.

The discus thrower's goal is to throw for maximum distance. In accordance with the capability provided by this invention, he correctly assumes that if he can maximize the velocity of a sensor placed on the back of his throwing hand he would achieve the greatest distance. Such a sensor location measures speed of the arm plus speed added by proper wrist action. To perfect the throwing technique, the user selects the velocity parameter, positions the sensor as previously discussed, and orient the arrow so that it pointed in the direction of the discus release.

To those skilled in the art, the invention admits of many variations. For example, the invention is a system for monitoring a user-selected kinetic activity at user-selected points on the body and generating immediate biofeedback information to the user. The system consists of at least one motion transducer that detects either linear motion in some form, or joint motion or flexure, and means such as universal appliances for emplacing or attaching the transducers at the various points on the body with appropriate orientations to sense the motion. The system includes a signal processing circuit for processing inputs coming from the transducers. The circuit has a signal measurement value step scale of 2 to 10 consecutive steps, preferably 3 to 5 steps. Each successive step or threshold level has a corresponding audio tone, and each successive tone is 1/3 to 1/1 octave higher in pitch than the preceding tone. The system has an audio tone generator circuit for generating the audio tones.

The system also has an adjustment for calibrating the step scale to the range of kinetic activity value to be recognized. The transducers are connected to the signal processing circuit, where the processing of inputs includes comparing the result to the step scale value during each cycle of kinetic activity. The occurrence of a result equaling a step value causes the corresponding audio tone to be generated by the tone generator. The circuitry recognizes and prolongs the sounding of the highest pitch of the audio tones occurring within a cycle of the kinetic activity for at least 0.1 seconds so that the user will recognize and retain the information. The connection of the transducers to the signal processing circuit may be hard wired, or use a wireless link.

The system may have output signals rather than audio tones and an output signal generator rather than an audio tone generator, and transmit or conduct the output signals to other presentation or recording equipment such as an audio panel, lamp display, crt, or computer. Alternatively, the system may include output signals in addition to audio tones, and an output signal generator in addition to the audio tone generator, directing the output signals to other presentation or recording equipment.

While the system works with a single transducer, there may be multiple transducers, with processing circuitry that can integrate multiple inputs and generate a composite result as a function of the multiple inputs. The transducers will likely have a bandwidth inclusive of the 0.1 to 40 hertz range of most kinetic activities. The system may have a voice actuated operator interface for enabling the system on command, and a timing circuit for disabling the system after a pre-determined short period of operation, typically in the order of 1 to 20 seconds, depending on the activity.

As another example, the system includes a series of mounting appliances that may be of any known or novel design, that fit or are adaptable to limbs, joints, and anywhere on bodies of persons of all sizes, for emplacing transducers. The appliances typically have multiple, cooperative ways to mount and orient the transducers for suitable sensitivity. The locations on an appliance can be color or number coded or the like, to distinguish one from another and provide assurance of repeatable placement of sensors. There may be pockets or slots incorporated into the appliance, where the pockets are sized for closely fitted insertion of transducers. There may also be a section of surface area suitable for emplacement and support of an electronic circuits housing or module, where the housing and the section are configured with mating components of a fastener system.

As yet another example, the system may include a sensor consisting of a beam structure instrumented with a wide area flexure sensing element, where the beam structure is planar and thin in shape, and the sensing element has a flexible output conductor. A trident shaped sensor mounting element, where the sensor is glued to or mounted in a pocket structure or otherwise attached at the distal end of the central prong, and the flexible output conductor is generally aligned with and running up said central prong. There is also an appliance attachable to a selected body joint, configured to accept the user selected emplacement of the trident shaped sensor mounting element in a manner that places the sensor over the joint at the inner or outer radius of flexure. The trident shaped sensor mounting element can be adaptable or adapted to support the signal processing circuit or its housing.

As still yet another example, there is a transducer module for sensing a kinetic activity at a selected point on the body with a high degree of directional selectivity, that has at least two directional motion sensor elements mounted orthogonal to one another, the ratio of gain of their respective outputs being adjustable for electronic selection of the effective axis of directional sensitivity.

As even still yet another example, there is a sensor system for sensing rotational kinetic activity of a user selected section of the body, having at least two directional motion sensors mounted on opposite sides of the body section in a plane normal to the axis of the section, with directional orientations of the sensors being arranged as tangent to the section. The outputs of the sensors are connected differentially for measuring rotation of the section about the axis. This sensor system can have independently adjustable gains of the sensors for selecting the placement of the measured axis of rotation as between the sensors.

As an additional example, there is a sensor system for sensing lateral motion in a user-selected direction of a user-selected section of the body during a kinetic activity, where at least two directional motion sensors are mounted on opposite sides of the section in a plane normal to the axis of the section, with their directional orientations parallel to the selected direction, and their outputs connected additively for canceling components of rotation of the section about the axis. There may be independently adjustable gains for the sensors for selecting placement of the measured axis of rotation as between said sensors.

As a yet additional example of the invention, there is a method for training to improve one's form in a selected kinetic activity, such as a golf swing or a rachet swing, utilizing a biofeedback system of the invention, consisting of the steps of selecting a desired pattern of kinetic activity for improvement, selecting principle points and directions of motion and flexure occurring during the conduct of the pattern, emplacing transducers at at least one principle point, calibrating the step scale of the system to a level of conduct presently within the user's capability, practicing the pattern until the biofeedback system indicates repeatable satisfactory performance at that level, recalibrating the threshold level of the step scale to a slightly higher level of competency of conduct, then repeating the steps of practicing and recalibrating until a final level of performance is achieved.

The objects and advantages of the invention may be further realized and attained by means of the instrumentalities and combinations particularly pointed out in the appended claims. Accordingly, the drawing and description are to be regarded as illustrative in nature, and not as restrictive.

I claim:

1. A system for monitoring a user selected kinetic activity at user selected points on the body and generating immediate biofeedback information to the user, comprising:

means for emplacing transducers at the user selected points on the body, a signal processing circuit for processing of inputs from said transducers, said circuit having a signal measurement value step scale of 2 to 10 consecutive steps, preferably 3 to 5 steps, each successive step having a corresponding audio tone, each successive tone being 1/3 to 1/1 octave higher in pitch than the preceding tone, an audio tone generator circuit for generating said audio tones, means for calibrating said step scale to the range of kinetic activity value to be recognized, at least one motion sensing transducer, said motion sensing transducer having a connection to said signal processing circuit, said processing of inputs further comprising comparing the result to said step scale value during a cycle of said kinetic activity, the occurrence of a said result equaling a step value causing the generation of said corresponding audio tone, means for maintaining the highest pitch of any said audio tone occurring within said cycle of said kinetic activity for at least 0.1 seconds.

2. The system of claim 1, said connection to said signal processing circuit comprising a wireless link.

3. The system of claim 1, comprising output signals rather than audio tones and an output signal generator rather than an audio tone generator, said output signals directed to other presentation or recording equipment.

4. The system of claim 1, further comprising output signals in addition to said audio tones and an output signal generator in addition to said audio tone generator, said output signals directed to other presentation or recording equipment.

5. The system of claim 1, said at least one motion sensing transducer being multiple transducers, said means for processing comprising means for integrating multiple inputs and generating a composite result as a function of said multiple inputs.

6. The system of claim 1, said at least one motion sensing transducer having a bandwidth inclusive of 0.1 to 40 hertz.

7. The system of claim 1, further comprising a voice actuated operator interface for enabling the system on command, and a timing circuit for disabling the system after a pre-determined short period of operation.

8. A system for monitoring user selected kinetic activity at user selected points on the body and generating immediate biofeedback information to the user, comprising:

means for emplacing transducers at said user selected points on the body, said means for emplacing transducers comprising a series of appliances in a range of sizes, said appliances attachable to body members and joints and having multiple, cooperative means for accepting user selected emplacements of said transducers, location of each said means on an appliance being coded for reference and repeatability, a signal processing circuit for processing of inputs from said transducers, said circuit having a signal measurement value step scale of 2 to 10 consecutive steps, preferably 3 to 5 steps, each successive step having a corresponding audio tone, each successive tone being 1/3 to 1/1 octave higher in pitch than the preceding tone, an audio tone generator circuit for generating said audio tones, means for calibrating said step scale to the range of kinetic activity value to be recognized, at least one motion sensing transducer, said motion sensing transducer having a connection to said signal processing circuit, said processing of inputs further comprising comparing the result to said step scale value during a cycle of said kinetic activity, the occurrence of a said result equaling a step value causing the generation of said corresponding audio tone, means for maintaining the highest pitch of any said audio tone occurring within said cycle of said kinetic activity for at least 0.1 seconds.

9. The system of claim 8, said multiple cooperative means comprising pockets incorporated into said appliance, said pockets sized for closely fitted insertion of a said transducer.

10. The system of claim 8, said multiple cooperative means comprising a section of surface area suitable for emplacement and support of an electronic circuits housing, said housing and said section configured with mating components of a fastener system.

11. The system for monitoring a user selected kinetic activity of claim 1, said motion sensing transducer being a transducer module for sensing a kinetic activity at a selected point on said body with a high degree of directional selectivity, said module comprising at least two directional motion sensor elements mounted orthogonal to one another, the ratio of gain of respective outputs of said sensor elements being adjustable for electronic selection of effective axis of directional sensitivity.

12. The system for monitoring a user selected kinetic activity of claim 1, said at least one motion sensing transducer being a sensor system for sensing rotational kinetic activity of a user selected section of said body, said sensor system comprising at least two directional motion sensors mounted on opposite sides of said section in a plane normal to the axis of said section with directional orientations tangent to said section, outputs of said sensors connected differentially for measuring rotation of said section about said axis.

13. The system for monitoring a user selected kinetic activity of claim 12, further comprising independent adjustability of gains of said sensors for selecting placement of measured axis of rotation as between said sensors.

14. The system for monitoring a user selected kinetic activity of claim 1, said at least one motion transducer being a sensor system for sensing lateral motion in a user selected direction of a user selected section of the body during a kinetic activity, said sensor system comprising at least two directional motion sensors mounted on opposite sides of said section in a plane normal to the axis of said section with directional orientations parallel to said selected direction, outputs of said sensors connected additively for canceling components of rotation of said section about said axis.

15. The system for monitoring a user selected kinetic activity of claim 14, further comprising independent adjustability of gains of said sensors for selecting placement of measured axis of rotation as between said sensors.

\* \* \* \* \*